United States Patent [19]
Guillaumet et al.

[11] Patent Number: 5,322,944
[45] Date of Patent: Jun. 21, 1994

[54] PROCESS FOR THE SYNTHESIS OF ENANTIOMERS OF 3-AMINOCHROMAN COMPOUNDS

[75] Inventors: Gérald Guillaumet, Orleans; Claude Fugier, Le Havre; Jean-Claude J. Souvie, Bolbec; Gérard Adam, Le Mesnil le Roi; Pierre Renard, Versailles; Daniel-Henri Caignard, Paris, all of France

[73] Assignee: Adir et Compagnie, Courbevoie, France

[21] Appl. No.: 906,572

[22] Filed: Jun. 30, 1992

[30] Foreign Application Priority Data

Jul. 1, 1991 [FR] France ............... 90 08147

[51] Int. Cl.$^5$ .......... C07D 471/10; C07D 405/12; C07D 335/06; C07D 417/12
[52] U.S. Cl. .......... 546/17; 546/116; 548/209; 548/221; 548/426; 548/431; 548/435
[58] Field of Search .......... 546/17

[56] References Cited

PUBLICATIONS

Chemical Abstracts, vol. 116(No. 5) abst. No. 41307(n) Feb. 3, 1992.

*Primary Examiner*—Alan L. Rotman
*Attorney, Agent, or Firm*—Gordon W. Hueschen

[57] ABSTRACT

Process for preparing enantiomers of general formula (I):

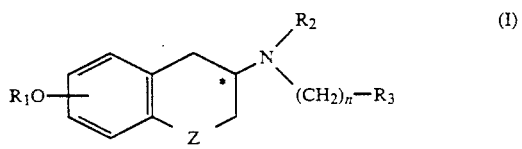

where Z, $R_1$, $R_2$, $R_3$ and n are defined in the description.

The compounds obtained according to the invention are useful as medicinal products.

14 Claims, No Drawings

PROCESS FOR THE SYNTHESIS OF ENANTIOMERS OF 3-AMINOCHROMAN COMPOUNDS

The present invention relates to a new process for the synthesis of enantiomers of 3-aminochroman compounds.

More specifically, the present invention relates to a new process for the synthesis of enantiomers of compounds of general formula (I):

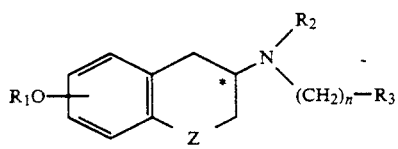

in which:

Z represents an oxygen atom or a sulfur atom, $R_1$ represents a hydrogen atom, a linear or branched ($C_1$–$C_6$) alkyl group, $R_2$ represents a hydrogen atom or a linear or branched ($C_1$–$C_6$) alkyl group, n is an integer between 1 and 6, $R_3$ represents a nitrile group, an amino group which is optionally substituted by:

- a linear or branched acyl group containing 2 to 7 carbon atoms,
- an alkylsulfonyl group,
- an arylsulfonyl group which is optionally substituted by an alkyl, alkoxy or hydroxyl group or by a halogen atom,
- a linear or branched ($C_1$–$C_6$) alkyl group, or $R_3$ represents any one of the following groups:

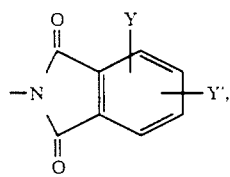

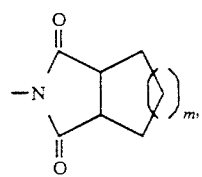

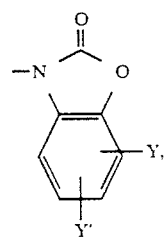

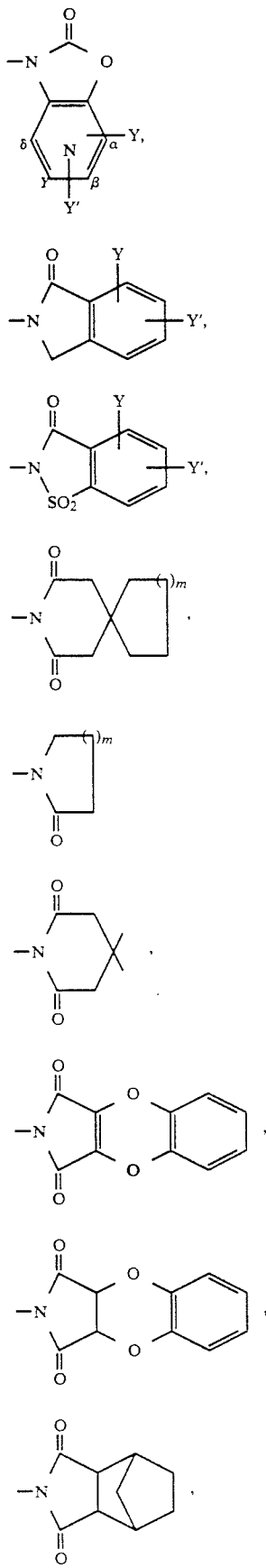

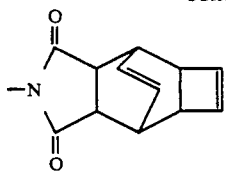

in which

Y and Y', which are identical or different, represent a hydrogen atom, a halogen atom, an alkyl, alkoxy or hydroxyl group, m is an integer equal to 1 or 2, and the nitrogen of the pyridine ring is situated in the α, β, γ or δ position of the ring junction, their enantiomers, diastereoisomers and epimers as well as their addition salts with a pharmaceutically acceptable acid.

The compounds of formula (I) as well as their addition salts with a pharmaceutically acceptable acid have useful pharmacological properties.

Binding assays have shown that the compounds of formula (I) behave as very potent 5-$HT_1A$ receptor ligands, with an agonist or antagonist activity at a level of the central nervous system. This very high affinity is accompanied by a very high selectivity towards these receptors compared with the $D_2$ and $\alpha_2$ receptors.

The compounds of formula (I) find their application in the treatment of stress, anxiety, depression, schizophrenia and pain, cardiovascular diseases and hypertension. They can also modify dietary and sexual behavior.

The compounds of formula (I) possess an asymmetric carbon carrying the nitrogen-containing functional group and therefore exist in the form of two isomers which, according to the nomenclature introduced by R. S. Cahn, Sir C. Ingold and V. Prelog, are termed (R) and (S).

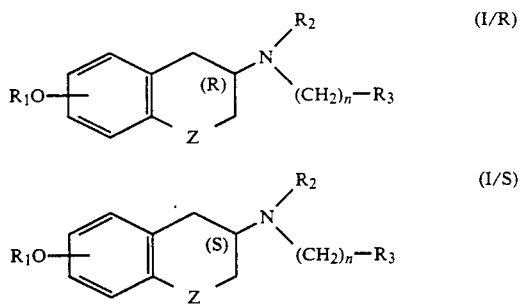

The activities of the compounds of formula (I/R) and (I/S) are quite different. The configuration of the asymmetric carbon causes substantial modifications in the affinity and the selectivity of the relevant product towards the various categories of receptors and consequently, on its pharmacological activity and its side effects. For example, the compound of formula (II):

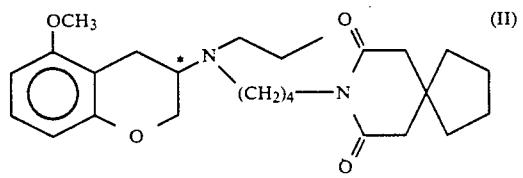

exists in the form of two enantiomers R and S whose specific rotation is evidently different. This specific rotation is noted (+) or (−) depending on whether the enantiomer deflects polarized light to the right or to the left.

If conventional binding techniques are used, the affinity of the (+) isomer of the compound of formula (II), expressed as K 0.5, is $2 \times 10^{-10}$ for the 5$HT_1A$ receptors and $2 \times 10^{-8}$ for the $D_2$ receptors, which is equivalent to a selectivity of the order of 100.

In the case of the (−) isomer, the Ki is $2 \times 10^{-9}$ for the 5$HT_1A$ receptors and $10^{-8}$ for the $D_2$ receptors, which is equivalent to a selectivity of the order of 5.

Consequently, the affinity of the (+) isomer for the 5$HT_1A$ receptors is about 10 times higher than that of the (−) isomer and the specificity is 20 times better.

It is therefore essential, in the case of these compounds, to be able to use a synthesis process which enables one of these two enantiomers to be selectively obtained.

Processes for the synthesis of the racemates of the compounds of formula (I) have been described in Application FR 90,04481.

However, Application FR 90,04481 performs the separation of the isomers at the level of 3-amino-2-chroman which is the raw material, and continues the synthesis from the enantiomer chosen. Now, the separation is a complex stage which is costly in terms of product, and performing a synthesis from raw materials which need to be resolved beforehand is not industrially viable since it is very costly. There is loss of raw material and therefore financial loss at each stage of the synthesis, the yields never being totally quantitative.

The Applicant has now discovered the means for improving this synthesis by performing the separation of the enantiomers only at the stage corresponding to the products of formula (I), which is the final stage of the synthesis.

To this end, the Applicant uses a raw material with a chroman structure lacking an asymmetric carbon, such as a known chromanone or its sulfur-containing homolog, and which is of low cost price.

The process according to the invention is more specifically one in which a compound of general formula (III):

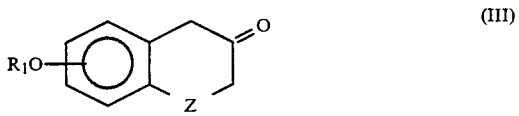

where $R_1$ and Z are as defined in formula (I), which is described in Patent Application EP-0,222,996, is used as raw material, and which compound is subjected to reductive amination preferably at ambient temperature and pressure in the presence of a catalyst, with a compound of general formula (IV):

where n and $R_3$ are defined as in formula (I), to give a compound of formula (V):

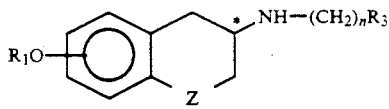

where $R_1$, $R_3$, Z and n are defined as above, which is a specific example of the compounds of formula (I) for which $R_2$ represents a hydrogen atom, the (+) and (−) isomers of which are separated by forming an organic solution and by adding an optically active acid thereto, preferably chosen from citric, tartaric, diacyl tartaric, maleic, malic, tosyl glutamic, camphorsulfonic, camphoric, camphanic, mandelic or quinic acid, and then subjecting to crystallization and separation of the two enantiomers, one precipitating and the other remaining in suspension, thus permitting their separation, the chosen isomer is treated, when, in the compound of formula (I) which it is desired to obtain, $R_2$ represents a linear or branched $C_1$-$C_6$ alkyl group, with a compound of formula (VI):

in which X represents a halogen atom and $R'_2$ represents a linear or branched $C_1$-$C_6$ alkyl group, specifically to give one enantiomer of the compound of formula (I).

A variant of the process according to the invention consists, when, in the compound of formula (I) which it is desired to obtain, $R_2$ represents a $C_1$-$C_6$ alkyl group, in treating the compound of formula (V) as defined above with a compound of formula (VI) as defined above, to give a compound of formula (I) in the form of a racemate, the (+) and (−) isomers of which are separated in a manner similar to that described above in a general manner, to give the compounds of formula (V).

The optically active acid salts with the compounds of formula (I) are new and form part of the invention as intermediates which are useful for its implementation.

The examples below illustrate the invention and do not imply any limitation thereto.

The preparation does not form part of the invention but is used for implementing the process according to the invention.

PREPARATION

5-Methoxy-3,4-Dihydro-[2H]-1-Benzopyran-3-One 0.4 ml of triethylamine is added to 0.5 g (2.4 mmol) of 3-carboxy-5-methoxy-2H-1-benzopyran, obtained as described in Application PCT 88/04654, in 5 ml of dichloromethane, followed dropwise by 0.65 g (2.4 mmol) of diphenylphosphoryl azide [$(C_6H_5O)_2P(O)N_3$] in solution in 2 ml of toluene. The solution is heated to 60° C. in order to distil off the dichloromethane, and 5 ml of anhydrous toluene are added. The reaction mixture is then heated, with stirring at 80°-85° C., for 1 h 30 min, and then 4 ml of a 6N solution of hydrochloric acid are added. The mixture is refluxed again for 2 hours and then cooled to ambient temperature. The product is then extracted several times with dichloromethane and the extraction solvent is dried over $MgSO_4$ and then evaporated under reduced pressure.

Purification of the crude sample obtained, by chromatography on a silica column (eluent $CH_2Cl_2$), enables 0.246 g (57%) of the expected product to be obtained in the form of an oil which subsequently becomes crystalline at 4° C. (m.p.=53°-54° C.).

5-Methoxy-3,4-dihydro-2H-1-benzopyran-3-one may also be prepared as indicated in European Patent Application EP-0,222,996.

EXAMPLE 1

(+)-3-[4-[N-(5-Methoxychroman-3-Yl)Amino]Butyl]-2,4-Dioxo-3-Azaspiro[4.5]Decane

Stage A:
3-[4-[N-(5-Methoxychroman-3-Yl)Amino]butyl]-2,4-Dixo-3-Azaspiro[4.5]Decane (Hydrochloride)

0.04 mole of 5-methoxychroman-3-one is dissolved in 10 ml of ethanol. At the same time, 1 g of N-(4-aminobutyl)-8-azaspiro[4.5]decane 7,9-dione hydrochloride is dissolved in 10 ml of ethanol, and the solution of chromanone obtained above is added to this solution. 0.16 g of sodium hydroxide in solution in 10 ml of ethanol is then added thereto. The mixture is stirred for one hour at ambient temperature, filtered and placed in a hydrogenating apparatus. 0.5 g of palladized carbon is added, the apparatus is purged with nitrogen and then with hydrogen, and the mixture is hydrogenated at ambient temperature and pressure. The mixture is filtered and the filtrate is evaporated to dryness. The residue is taken up in ethyl acetate and gaseous hydrochloric acid is added thereto. The mixture is allowed to precipitate and is drained.

Yield: 70%

Stage B:
(+)-3-[4-[N-(5-Methoxychroman-3-Yl)Amino]Butyl]-2,4-Dioxo-3-Azaspiro[4.5]Decane (Hydrochloride)

The product obtained in the preceding stage is dissolved in 17 ml of ethanol and 0.03 mole of L-(−)-malic acid dissolved in 12.5 ml of ethanol is added. The mixture is stirred for 30 minutes. It is allowed to stand at low temperature. The precipitate formed is drained and dried.

Specific rotation $[\alpha]_D^{21}$ (1%, $CHCl_3$): +15.3°

EXAMPLE 2

(+)-3-[4-[N-n-Propyl-N-(5-Methoxychroman-3-Yl)Amino]Butyl]-2,4-Dioxo-3-Azaspiro[4.5]Decane (Oxalate)

1.5 mmol of the compound prepared in Example 1 are dissolved in 10 ml of dimethylformamide in the presence of 4.4 mmol of 1-iodopropane and 4.4 moles of potassium carbonate. After stirring for 24 hours at 60° C., the solvent is evaporated and the crude reaction mixture is taken up in 10 ml of water and extracted with dichloro-methane. The organic phase is dried and evaporated and the expected product is obtained after purification by chromatography on a silica column. It is salified with oxalic acid.

Yield: 83%

Specific rotation $[\alpha]_D^{21}$: +50°

EXAMPLE 3

(−)-3-[4-[N-(5-Methoxychroman-3-Yl)Amino]Butyl]-2,4-Dioxo-3-Azaspiro[4.5]Decane (Hydrochloride)

By carrying out the procedure as in Example 1, but replacing L-(−)-malic acid by D-(+)-malic acid, the title product is obtained.

EXAMPLE 4

(−)-3-[4-[N-n-Propyl-N-(5-Methoxychroman-3-Yl)Amino]Butyl]-2,4-Dioxo-3-Azaspiro[4.5]Decane (Oxalate)

By carrying out the procedure as in Example 2, but replacing the product obtained in Example 1 by the product obtained in Example 3, the title product is obtained. It is salified with oxalic acid.

Specific rotation $\alpha_D$ of the free amine $[\alpha]_D^{21}$: −50 (4% CHCl$_3$)

EXAMPLE 5

(+)-3-[4-[N-(5-Methoxychroman-3-Yl)Amino]Butyl]-2,4-Dioxo-3-Azaspiro[4.5]Decane (Hydrochloride)

2 g of the product obtained in Example 1, stage A, are dissolved in 3 cm$^3$ of ethanol. A solution of 1.08 g of (−)-camphanic acid in 1.6 cm$^3$ of ethanol is added to this solution. The mixture is stirred for 30 minutes. It is allowed to stand at low temperature. The precipitate formed is drained and dried.

By carrying out the procedure as in the preceding examples without salifying either with hydrochloric acid or with oxalic acid, and by using the appropriate compound of formula NH$_2$—(CH$_2$)$_n$—R$_3$, the following are similarly obtained:

(+)-5-Methoxy-3-[4-[N-n-Propyl-N-2-(4-Toluenesulfonylamino)Ethyl]Amino]Chroman

Specific rotation $[\alpha]_D^{21}$ (4%, CHCl$_3$): +44°

(−)-5-Methoxy-3-[N-n-Propyl-N-[2-(4-Toluenesulfonylamino)Ethyl]Amino]Chroman and the diastereoisomers of the following compounds:

5-Methoxy-3-[N-n-Propyl-N-[4-(4-Toluenesulfonylamino)Butyl]Amino]Chroman
  Specific rotation of the (+) diastereoisomer, $[\alpha]_D^{21}$ (4%, CHCl$_3$): +52°

3-[4-[N-(5-Methoxychroman-3-Yl)Amino]Butyl]-2,4-Dioxo-3-Azabicyclo[3.3.0]Octane

3-[4-[N-n-Propyl-N-(5-Methoxychroman-3-Yl)Amino]Butyl]-2,4-Dioxo-3-Azabicyclo[3.3.0]Octane
  Specific rotation of the (+) diastereoisomer, $[\alpha]_D^{21}$ (4%, CHCl$_3$): +57°

3-[4-[N-(5-Methoxybenzothiopyran-3-Yl)Amino]Butyl]-2,4-Dioxo-3-Azaspiro[4.5]Decane 3-[4-[N-n-Propyl-N-(5-Methoxybenzothiopyran-3-Yl)Amino]Butyl]-2,4-Dioxo-3-Azabicyclo[4.5]Decane 5-Methoxy-3-[N-n-Propyl-N-[2-(4-Toluenesulfonylamino)Ethyl]Amino]-3,4-Dihydro-[2H]-1-benzothiopyran 5-Methoxy-3-[N-n-Propyl-N-[4-(4-Toluenesulfonylamino)Butyl]Amino]-3,4-Dihydro-[2H]-Benzothiopyran 5-Methoxy-3-[N-n-Propyl-N-[3-(4-Toluenesulfonylamino)Propyl]Amino]-3,4-Dihydro-[2H]-Benzothiopyran

We claim:

1. A process for the synthesis of enantiomers of compounds of the formula (I):

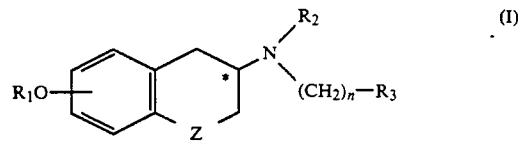

in which:

Z represents an oxygen atom or a sulfur atom, or
R$_1$ represents a hydrogen atom, a linear or branched (C$_1$-C$_6$) alkyl group,
R$_2$ represents a hydrogen atom or a linear or branched (C$_1$-C$_6$) alkyl group,
n is an integer from 1 to 6, inclusive
R$_3$ represents

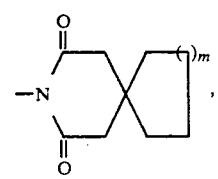

in which: m is an integer equal to 1 or 2, their enantiomers, diastereoisomers and epimers, as well as their addition salts with a pharmaceutically-acceptable acid, wherein a compound of formula (III):

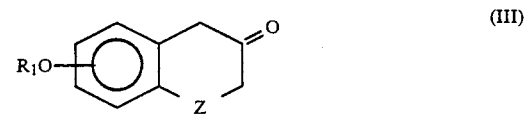

wherein R$_1$ and Z are defined as in formula (I), is subjected to reductive amination at ambient temperature and pressure in the presence of a catalyst, with a compound of the formula (IV):

where n and R$_3$ are defined in formula (I), to give a compound of formula (V):

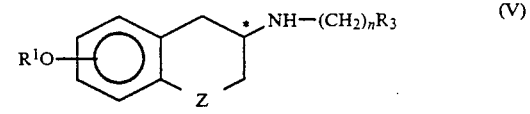

where R$_1$, R$_3$, Z and n are defined as above, which is a specific example of the compounds of formula (I) for which R$_2$ represents a hydrogen atom, the (+) and (−) isomers of which are separated by forming an organic solution therefore and by adding an optically-active acid thereto, thereby subjecting to crystallization, one of the two enantiomers crystallizing and the other remaining in solution, the chosen isomer is then treated, when, in the compound of formula (I) which it is desired to obtain, R$_2$ represents a linear or branched C$_1$-C$_6$ alkyl group, with a compound of formula (VI):

in which X represents a halogen atom and R'$_2$ represents a linear or branched C$_1$-C$_6$ alkyl group, specifically to give one enantiomer of the compound of formula (I).

2. A process for preparing enantiomers of compounds of formula (I) as claimed in claim 1, for which $R_2$ does not represent a hydrogen atom, wherein a compound of formula (V), as identified in claim 1, is reacted with a compound of formula (VI), as identified in claim 1, to give the racemate of a compound of formula (I), as identified in claim 1, the enantiomers of which are separated by forming an organic solution and by adding an optically-active acid thereto, and by subjecting solution to crystallization, one of the two enantiomers crystallizing, the other remaining in solution.

3. The process for preparing enantiomers of compounds of formula (I) as claimed in claim 1, wherein the acid used for the separation of the enantiomers is chosen from (+) or (−) citric, tartaric, diacetyl tartaric, maleic, malic, tosyl glutamic, camphorsulfonic, camphoric, camphanic, mandelic and quinic acid, depending on the enantiomer of the product desired.

4. The process for preparing enantiomers of compounds of formula (I) as claimed in claim 1, wherein the acid used for separating the isomers is (+)- or (−)-malic acid, depending on the enantiomer.

5. The process for preparing enantiomers desired of compounds of formula (I) as claimed in claim 1, wherein the acid used for separating the isomers is (+)- or (−)-camphanic acid, depending on the desired enantiomer.

6. The process for preparing, as claimed in claim 1, the compound of formula (I) which is (+)-3-[4-[N-(5-methoxychroman-3-yl)amino]butyl]-2,4-dioxo-3-azaspiro[4.5]decane and its addition salts with a pharmaceutically-acceptable acid.

7. The process for preparing, as claimed in claim 1, the compound of formula (I) which is (−)-3-[4-[N-(5-methoxychroman-3-yl)amino]butyl]-2,4-dioxo-3-azaspiro[4.5]decane and its addition salts with a pharmaceutically acceptable acid.

8. The process for preparing, as claimed in claim 1, the compound of formula (I) which is (+)-3-[4-[N-n-propyl-N-(5-methoxychroman-3-yl)amino]butyl]-2,4-dioxo-3-azaspiro[4.5]decane and its addition salts with a pharmaceutically-acceptable acid.

9. The process for preparing, as claimed in claim 1, the compound of formula (I) which is (−)-3-[4-[N-n-propyl-N-(5-methoxychroman-3-yl)amino]butyl]-2,4-dioxo-3-azaspiro[4.5]decane and its addition salts with a pharmaceutically-acceptable acid.

10. An addition salt of a compound of formula (I) and its enantiomers as set forth in claim 1, with an optically-active acid, that is to say possessing one or more asymmetric carbon atoms in its structure.

11. An addition salt of a compound of formula (I) and its enantiomers as set forth in claim 1, with (+) or (−) citric, tartaric, diacyl tartaric, maleic, malic, tosyl glutamic, camphorsulfonic, camphoric, camphanic, mandelic, and quinic acid.

12. An addition salt of the compound of formula (I) and its enantiomers as set forth in claim 1, with (+)- or (−)-malic acid.

13. An addition salt of the compound of formula (I) and its enantiomers as set forth in claim 1, with (+)- or (−)-camphanic acid.

14. The process of claim 1 wherein the reductive amination is carried out at ambient temperature and pressure and in the presence of a palladized carbon catalyst.

* * * * *

UNITED STATES PATENT AND TRADEMARK OFFICE
CERTIFICATE OF CORRECTION

PATENT NO. : 5,322,944
DATED      : June 21, 1994
INVENTOR(S) : Gérald Guillaumet, Claude Fugier, Jean-Claude J. Souvie, Gérard Adam, Pierre Renard, Daniel-Henri Caignard It is certified that error appears in the above-indentified patent and that said Letters Patent is hereby corrected as shown below:

```
Column 6, line 13; "Dixo" should read --Dioxo--
Column 8, line 10; delete "or".
Column 8, line 11; "atom, a" should read --atom, or a--.
Column 8, line 26; delete "an integer equal to ".
Column 8, line 56; "therefore" should read --thereof--.
Column 8, line 57; "subjecting to" should read --subjecting the
      solution to--.
Column 9, line 11; "subjecting solution" should read --subject-
      ing the solution--.
Column 9, line 24; "enantiomer." should read --enantiomer
      desired.--.
Column 9, line 28; delete "desired".
Column 9, line 29;              "tiomer." should read
      -- tiomer desired.--.
Column 10, line 24; "and" should read --or--.
Column 10, line 25; "the" should read --a--.
Column 10, line 28; "the" should read --a--.
```

Signed and Sealed this

Eleventh Day of October, 1994

Attest:

BRUCE LEHMAN

*Attesting Officer*    *Commissioner of Patents and Trademarks*